(12) United States Patent
Komata et al.

(10) Patent No.: US 6,608,217 B2
(45) Date of Patent: Aug. 19, 2003

(54) PROCESS FOR PRODUCING 4-SUBSTITUTED BENZOPYRAN DERIVATIVES

(75) Inventors: Takeo Komata, Saitama (JP); Masaki Fujiwara, Saitama (JP); Takanao Tarui, Saitama (JP); Yusuke Saito, Saitama (JP); Hiroshi Minesaki, Saitama (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 10/255,099

(22) Filed: Sep. 26, 2002

(65) Prior Publication Data

US 2003/0109574 A1 Jun. 12, 2003

(30) Foreign Application Priority Data

Sep. 28, 2001 (JP) ........................ 2001-300314
Oct. 30, 2001 (JP) ........................ 2001-332471

(51) Int. Cl.⁷ ........................ C07D 311/04; C07C 49/84; C07C 45/00
(52) U.S. Cl. ........................ 549/405; 568/314; 568/315; 568/337
(58) Field of Search ........................ 549/405; 568/314, 568/315, 337

(56) References Cited

FOREIGN PATENT DOCUMENTS

| DE | 2653601 | 6/1978 |
|---|---|---|
| WO | 00/18754 | 4/2000 |

OTHER PUBLICATIONS

Tadakatsu Takahashi, et al., "Synthesis and Vaorelaxant Activity of N–Imino–2–(Benzopyran–4–Yl) Pyridine K+ Channel Openers" Bioorganic & Medicinal Chemistry Letters, vol. 4, No. 24, 1994, pp. 2899–2902.

Ng. Ph. Buu–Hoi, et al., "Some Synthesis from p–Fluoro-anisole" Contribution from the Department of Organic Chemistry, Radium Institute, University of Paris, Apr. 21, 1954, pp. 1617–1621.

Hiroshi Koga, et al., "Synthesis of Key Intermediates Benzopyran–4–Carboxylic Acids of New Potassium Channel Openers Benzopyran–4–Amides Via Palladium–Catalyzed Hydroxycarbonylation" Tetrahedron Letters, vol. 36, No. 1, 1995, pp. 87–90.

Naoki Taka, et al., "6–Sbustituted 2,2–Bis(fluoromethyl)–benzopyran–4–carboxamide K+ Channel Openers" Bioorganic and Medicinal Chemistry, vol. 8, 2000, pp. 1393–1405.

M. Consuelo Jimenez, et al., "Norrish Type I Photoreaction in the Presence of Phenols; an Intermolecular Photo–Fries Rearrangement" J. Chem. Soc., 1995.

*Primary Examiner*—Amelia Owens
(74) *Attorney, Agent, or Firm*—Crowell & Moring LLP

(57) ABSTRACT

The present invention relates to a first process for producing a 2,2-bis(fluoromethyl)-6-(perfluoroalkyl)-2H-1-benzopyran-4-carboxylic acid. The first process includes the steps of (a) reacting a 2,2-bis(fluoromethyl)-6-(perfluoroalkyl)-2H-1-benzopyran-4-one with a perfluoroalkanesulfonic acid anhydride in the presence of a base, thereby obtaining a perfluoroalkanesulfonic 2,2-bis(fluoromethyl)-6-(perfluoroalkyl)-2H- 1-benzopyran-4-yl ester; and (b) reacting the benzopyranyl ester with carbon monoxide in the presence of a palladium complex compound and a base, thereby obtaining the carboxylic acid. The present invention further relates to a second process for producing a 2-hydroxy-5-(perfluoroalkyl) acetophenone, which can be a raw material for producing the carboxylic acid. The second process includes the steps of (c) reacting a 4-(perfluoroalkyl)alkoxybenzene with acetic anhydride or an acyl halide in the presence of a Lewis acid, thereby obtaining a 2-alkoxy-5-(perfluoroalkyl)acetophenone; and (d) dealkylating the 2-alkoxy-5-(perfluoroalkyl) acetophenone by a dealkylating agent.

18 Claims, No Drawings

PROCESS FOR PRODUCING 4-SUBSTITUTED BENZOPYRAN DERIVATIVES

BACKGROUND OF THE INVENTION

The present invention relates to a process for producing a 2,2-bis(fluoromethyl)-6-(perfluoroalkyl)-2H-1-benzopyran-4-carboxylic acid represented by the general formula [1], which is a 4-substituted benzopyran derivative useful as an intermediate for medicines and agricultural chemicals,

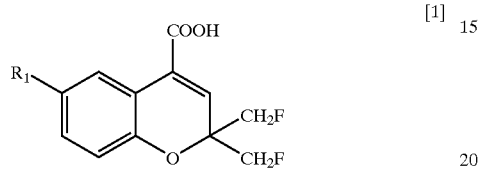

[1]

wherein $R_1$ is a perfluoroalkyl group that is represented by $C_nF_{2n+1}$ where n is an integer of 1–10 and that optionally has a branch in a carbon structure of the perfluoroalkyl group.

It is disclosed in WO/00/18754 and Bioorganic and Medicinal Chemistry 8 (2000), 1393–1405 that the above carboxylic acid can be synthesized by five (5) steps from a starting material of 2,2-bis(fluoromethyl)-6-(perfluoroalkyl)-2H-1-benzopyran-4-one (represented by the general formula [2]; hereinafter referred to "benzopyranone [2]" for simplification) via 4-bromo- 2,2- bis(fluoromethyl)-6-(perfluoroalkyl)-2H- 1-benzopyran (represented by the general formula [11]),

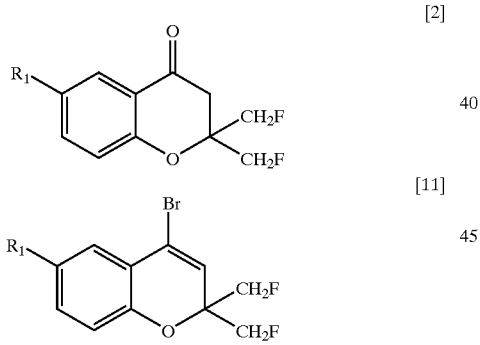

where $R_1$ is defined as above. Hereinafter, various compounds may be referred to for simplification in a manner similar to that the benzopyranone represented by the general formula [2] is referred to as the benzopyranone [2]. As shown by the following scheme, the five steps are explained in more detail. At first, the benzopyranone [2] is reduced in the first step by sodium borohydride or the like. The resulting benzopyranol [12] is dehydrated in the second step by a dehydrating agent (e.g., p-toluenesulfonic acid). The resulting benzopyran derivative [13] is brominated in the third step by bromine. The resulting dibromobenzopyran [14] is reacted in the fourth step with a base. The resulting 4-bromobenzopyran [11] is reacted in the fifth step with carbon monoxide in the presence of a palladium complex compound and a base to obtain the benzopyran carboxylic acid [1],

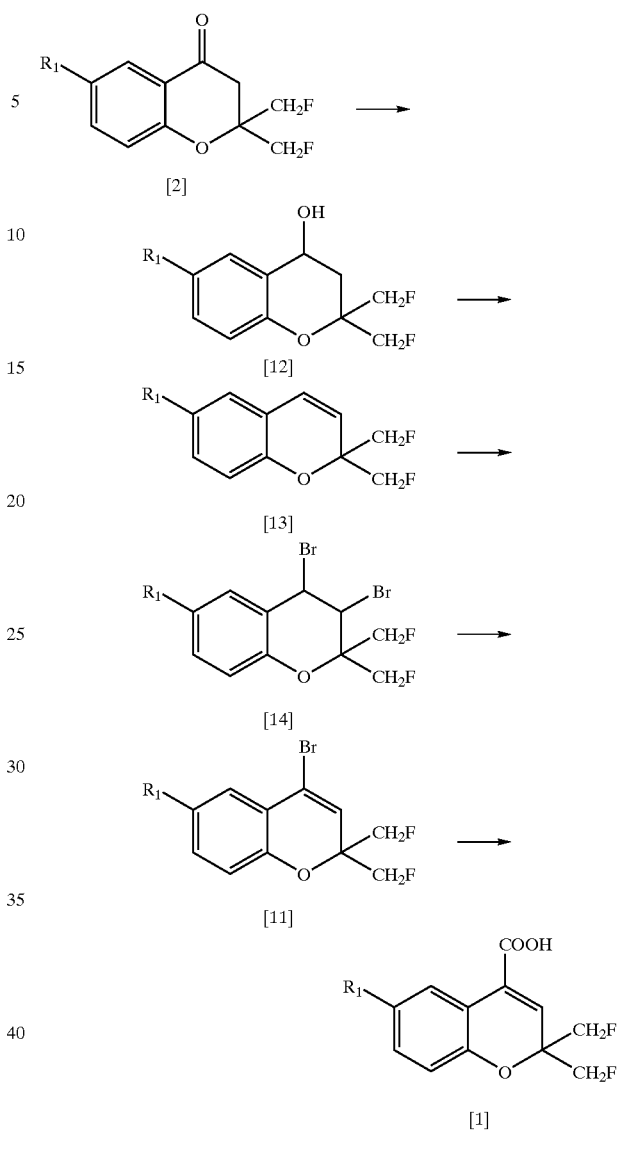

where $R_1$ is defined as above.

It is further disclosed in WO/00/18754 that the 4-bromobenzopyran [1] is obtained by four steps from a 3,4-dihalogeno-1-perfluoroalkylbenzene [15], that it is obtained by four steps from an acetylene derivative [16], and that it is obtained by subjecting an acetylene derivative [17] to a thermal cyclization,

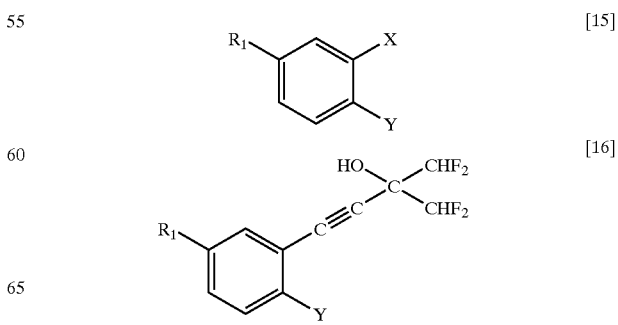

-continued

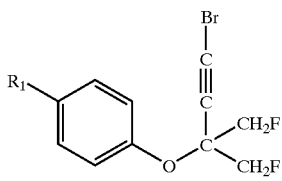

[17]

where $R_1$ is defined as above, and X and Y are independently halogen atoms.

Of the above-mentioned conventional processes, one using the benzopyranone [2] as a starting material has advantages over others in terms of reagents availability and selectivity of the reaction. However, even that process requires taking the above-mentioned five steps to obtain the benzopyran carboxylic acid [1], thus making it cumbersome. Therefore, there is a demand for a process for producing the benzopyran carboxylic acid with fewer steps.

The present invention further relates to a process for producing hydroxyacetophenones, which are useful as intermediates for medicines and agricultural chemicals, and particularly to 2-hydroxy-5-(perfluoroalkyl)acetophenones.

There are known the following two (2) processes for producing a 2-hydroxy-5-(perfluoroalkyl)acetophenone represented by the general formula [5],

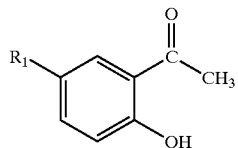

[5]

where $R_1$ is defined as above.

DE 2653601 A1 discloses that 2-hydroxy-5-(trifluoromethyl)acetophenone was obtained by mixing together 4-(trifluoromethyl)phenol and hydrofluoric acid anhydride, then by adding acetyl chloride to the mixture, and then by heating the mixture at 100° C. under a pressurized condition.

J. Chem. Soc., Chem. Commun. (1995) 19, 2009–10 discloses that 4-(trifluoromethyl)phenol and pinacolone were dissolved in benzene, followed by irradiation with light, thereby obtaining 2-hydroxy- 5-(trifluoromethyl) acetophenone with a yield of about 13%.

In general, benzene rings having a perfluoroalkyl group (e.g., trifluoromethyl group and pentafluoroethyl group) are low in reactivity in Friedel-Crafts type electrophilic substitution reactions. Thus, it is necessary to have a severe condition, for example, by heating at 100° C. or higher or by light irradiation in the presence of a strong acid or strong base in order to directly introduce an acyl group onto 4-perfluoroalkylphenol by Friedel-Crafts reactions. Such severe condition, however, may gradually decompose the perfluoroalkyl group, thereby lowering selectivity of the target reaction. This may lower the yield of 2-hydroxy-5-(perfluoroalkyl)acetophenone or may makes it difficult to conduct purification by adverse effects of by-products.

Thus, there is a demand for processes for producing 2-hydroxy-5-(perfluoroalkyl)acetophenones in an industrial manner with a mild reaction condition.

SUMMARY OF THE INVENTION

It is therefore an object of the present invention to provide a process for efficiently producing a 2,2-bis(fluoromethyl) -6-(perfluoroalkyl)- 2H- 1 -benzopyran-4-carboxylic acid.

It is another object of the present invention to provide a process for producing 2-hydroxy-5-(perfluoroalkyl) acetophenones in an industrial manner under a mild reaction condition.

According to a first aspect of the present invention, there is provided a novel first process for producing a 2,2-bis (fluoromethyl)-6-(perfluoroalkyl)-2H- 1-benzopyran-4-carboxylic acid represented by the general formula [1]. The process comprises the steps of:

(a) reacting a 2,2-bis(fluoromethyl)-6-(perfluoroalkyl)-2H-1-benzopyran-4-one, represented by the general formula [2], with a perfluoroalkanesulfonic acid anhydride, represented by the general formula [3], in the presence of a base, thereby obtaining a perfluoroalkanesulfonic 2,2-bis(fluoromethyl)-6-(perfluoroalkyl)-2H-1-benzopyran-4-yl ester represented by the general formula [4]; and (b) reacting the benzopyranyl ester with carbon monoxide in the presence of a palladium complex compound and a base, thereby obtaining the carboxylic acid,

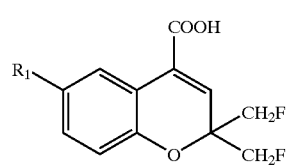

[1]

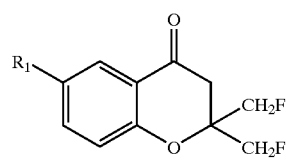

[2]

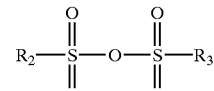

[3]

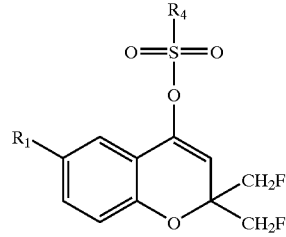

[4]

where $R_1$ is a perfluoroalkyl group that is represented by $C_nF_{2n+1}$ where n is an integer of 1–10 and that optionally has a branch in a carbon structure of the perfluoroalkyl group;

each of $R_2$ and $R_3$ is independently a lower perfluoroalkyl group that is represented by $C_nF_{2n+1}$ where n is an integer of 1–10 and that optionally has a branch in a carbon structure of the lower perfluoroalkyl group; and $R_4$ is identical with the $R_2$ or $R_3$.

Hereinafter, the 2,2-bis(fluoromethyl)-6-(perfluoroalkyl)-2H- 1-benzopyran-4-one, represented by the general formula [2], may be referred to as the benzopyranone [2] for simplification. Various other compounds may also be referred to in a manner similar to this.

It is disclosed in Bioorganic & Medicinal Chemistry 8 (2000) 1393–1405 that the benzopyranone [2], which is the starting material of the step (a), can be produced by the step (e) reacting a 2-hydroxy-5-(perfluoroalkyl) acetophenone, represented by the general formula [5], with 1,3-difluoroacetone in the presence of a base,

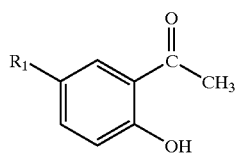

[5]

where $R_1$ is defined as above. Thus, in case that this reaction is conducted prior to the step (a), the acetophenone [5] can be the starting material for producing the carboxylic acid [1].

According to a second aspect of the present invention, there is provided a novel second process for producing such acetophenone [5]. The second process comprises the steps of:

(c) reacting a 4-(perfluoroalkyl)alkoxybenzene, represented by the general formula [6], with acetic anhydride or an acyl halide in the presence of a Lewis acid, thereby obtaining a 2-alkoxy-5-(perfluoroalkyl) acetophenone represented by the general formula [7]; and (d) dealkylating the 2-alkoxy-5-(perfluoroalkyl) acetophenone by a dealkylating agent, thereby obtaining the 2-hydroxy-5-(perfluoroalkyl) acetophenone,

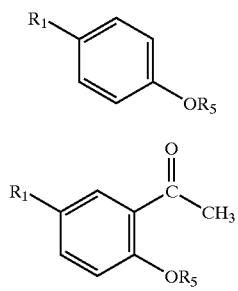

[6]

[7]

where $R_1$ is defined as above; and $R_5$ is a straight-chain or non-straight-chain alkyl group having a carbon atom number of 1–20. Thus, it is possible by the present invention to produce the carboxylic acid [1] from the alkoxybenzene [6] by sequentially conducting the steps of (c), (d), (e), (a) and (b).

Furthermore, it is possible by the present invention to produce the alkoxybenzene [6] by the step (f) reacting a 4-(perfluoroalkyl)phenol represented by the general formula [8] with an alkylation agent or reacting a 4-(perfluoroalkyl) halogenobenzene represented by the general formula [9] with a metal alcoholate.

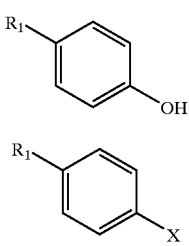

[8]

[9]

where $R_1$ is defined as above and X is a fluorine, chlorine, bromine or iodine. Thus, it is possible by the present invention to produce the carboxylic acid [1] from the phenol [8] or the halogenobenzene [9] by sequentially conducting the steps of (f), (c), (d), (e), (a) and (b), as shown by the following scheme in which the numbers represent the above-mentioned general formulas and in which the letters of "a" to "f" represent the above-mentioned steps.

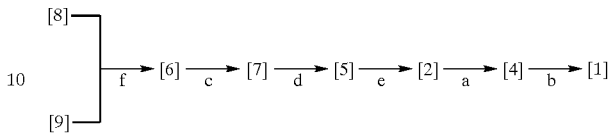

DESCRIPTION OF THE PREFERRED EMBODIMENTS

As stated above, it is possible by the first process to obtain the target product (i.e., the benzopyrancarboxylic acid [1]) from the benzopyranone [2] (starting material) by only the two steps of (a) and (b) without producing the 4-bromobenzopyran [11] as an intermediate.

In fact, the present inventors have found that it is possible to very smoothly obtain the sulfonic ester [4] by reacting the benzopyranone [2] with the perfluoroalkane-sulfonic acid anhydride [3] in the presence of a base (i.e., the step (a)) and that it is possible to easily obtain the target benzopyrancarboxylic acid [1] by reacting the sulfonic ester [4] (obtained by the step (a)) with carbon monoxide in the presence of a palladium complex compound and a base, as shown by the following reaction scheme.

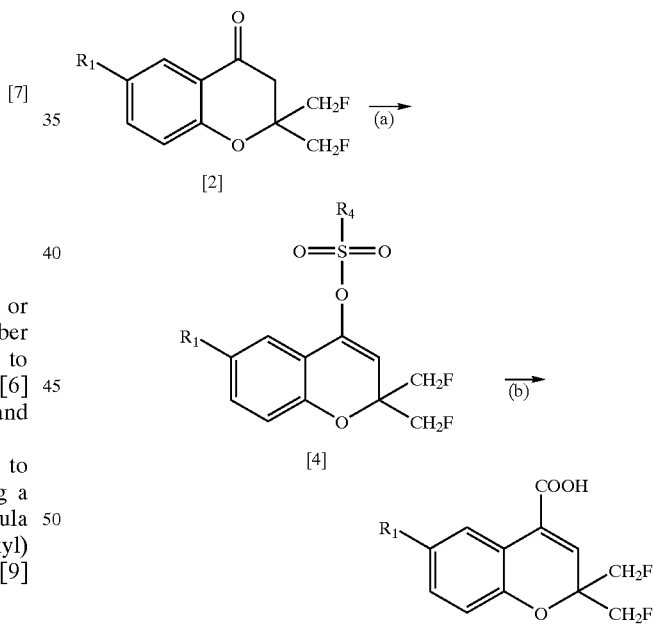

The first process according to the present invention will be described in detail in the following. As stated above, the substituent $R_1$ is a perfluoroalkyl group that is represented by $C_nF_{2n+1}$ where n is an integer of 1–10 and that optionally has a branch in its carbon structure. In view of its availability, n is preferably 1, 2 or 3. In this case, $R_1$ is trifluoromethyl group, pentafluoroethyl group, heptafluoro-n-propyl group, or heptafluoro-i-propyl group. Of these, trifluoromethyl group (where n=1) is particularly preferable in view of its availability and usefulness of the target product.

The step (a) may be conducted at a temperature of 0–100° C., preferably 0–60° C., more preferably 0–30° C.

It is necessary to conduct the step (a) in the presence of a base. The type of this base is not particularly limited. It is preferable to select the base from pyridines (e.g., pyridine, monomethylpyridines, dimethylpyridines, monoethylpyridines, trimethylpyridines, 2,6-di-tert-butyl-4-methylpyridine, and 4-dimethylaminopyridine (DMAP)). Although the amount of the base is not particularly limited, it is preferably 1–10 moles, more preferably 1–4 moles, per mol of the benzopyranone [2]. If it is less than 1 mol, the reaction may not proceed sufficiently. If it is greater than 10 moles, it may cause an economical disadvantage.

Examples of the sulfonic acid anhydride [3] are trifluoromethanesulfonic acid anhydride and pentafluoroethanesulfonic acid anhydride. In the general formula [3], $R_2$ and $R_3$ may be different perfluoroalkyl groups.

However, sulfonic acid anhydrides [3] having such $R_2$ and $R_3$ are generally high in price. Therefore, it is preferable to use one in which $R_2$ and $R_3$ are the same perfluoroalkyl groups. It is particularly preferable to use trifluoromethanesulfonic acid anhydride due to its availability. The amount of the sulfonic acid anhydride [3] used in the reaction may be 1–15 moles, preferably 1–5 moles, more preferably 1–3 moles, per mol of the benzopyranone [2]. If it is less than 1 mol, the reaction may not proceed sufficiently. If it is greater than 15 moles, it may cause an economical disadvantage.

It is preferable to use a solvent in the step (a). This solvent is not particularly limited. Its preferable examples include methylene chloride, chloroform, carbon tetrachloride, and 1,2-dichloroethane. Although the time for completing the step (a) may be approximately in a range of 10–200 hrs, it may deviate from this range depending on the reaction conditions. Therefore, it is preferable to terminate the reaction after confirming that the raw materials have been consumed sufficiently by monitoring the progress of the reaction using a conventional analytical technique such as liquid chromatography or thin layer chromatography.

The purification operation after the step (a) is not particularly limited and can be conducted by normal techniques in the field of organic synthesis. For example, the reaction mixture can be washed with water, followed by extraction with a low-boiling-point organic solvent, column chromatography, recrystallization, and removal of the solvent by distillation, thereby obtaining the sulfonic ester [4].

The benzopyranone [2] used in the step (a) is not limited at all with respect to its synthesis. For example, it is particularly economically preferable to obtain the benzopyranone [2] by the above-mentioned step (e) reacting the acetophenone [5] with 1,3-difluoroacetone in the presence of a base, as shown by the following scheme.

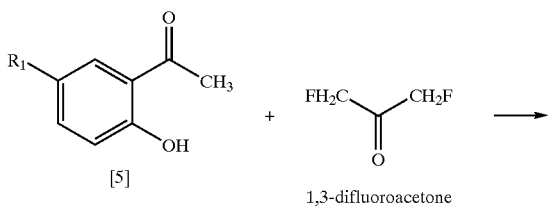

1,3-difluoroacetone

-continued

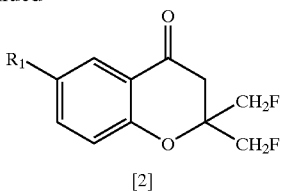

[2]

The step (e) can be conducted by mixing together the acetophenone [5], 1,3-difluoroacetone and a base, and then by stirring the mixture in the presence of a solvent at a temperature of preferably 0–60° C., more preferably 20–40° C., thereby synthesizing the benzopyranone [2]. For example, the base and the solvent are respectively pyrrolidine and methanol, but are not limited thereto. It is possible to achieve the reaction of the step (e) by mixing together 1 part by mole of the acetophenone [5], 1 part by mole of 1,3-difluoroacetone, and 1 part by mole of a base. The reaction is, however, not limited to these relative amounts. It is possible to improve conversion of the reaction by using the base and 1,3-difluoroacetone in slightly excessive amounts relative to that of the acetophenone [5]. For example, each of the former compounds may be in an amount of 1–5 moles, preferably 1–2 moles, per mol of the latter compound. The reaction mixture obtained by the step (e) may be subjected to a normal purification procedure of organic syntheses, thereby separating the target benzopyranone [2]. The step (e) and the subsequent purification procedure may be conducted in accordance with the disclosure of Bioorganic & Medicinal Chemistry 8 (2000), 1393–1405 and may be modified by a person skilled in the art.

The step (b) will be described in detail in the following. As stated above, the step (b) is conducted by reacting the sulfonic ester [4] with carbon monoxide in the presence of a palladium complex compound and a base, thereby obtaining the carboxylic acid [1]. The palladium complex compound is not particularly limited. Its examples include bis(dibenzylideneacetone)palladium ($Pd(dba)_2$), tris(dibenzylidene) (chloroform) dipalladium ($Pd_2(dba)_3$ ($CHCl_3$)), tetraquis(triphenylphosphine)palladium ($Pd(PPh_3)_4$), palladium acetate $Pd(OCOMe)_2$, $PdCl_2$, $PdBr_2$, $PdCl_2(PPh_3)_2$, $Pd(OCOMe)_2(PPh_3)_2$, $PdBr_2(PPh_3)_2$, $PdCl_2(PMe_3)2$, $PdCl_2[P(Ph)_2CH_2CH_2P(Ph)_2]$, $PdCl_2[P(Ph)_2CH_2CH_2CH_2P(Ph)_2]$, $PdCl_2[P(Ph)_2CH_2CH_2CH_2CH_2P(Ph)_2]$, and $Pd_2Br_4(PPh_3)_2$, where Me and Ph represent methyl group and phenyl group, respectively. The amount of the palladium complex compound used in the reaction may be 0.00001–0.5 moles, preferably 0.00005–0.1 moles, more preferably 0.0001–0.1 moles, per mol of the sulfonic ester [4]. If it is less than 0.00001 moles, the reaction rate may become too slow, making it disadvantageous to an industrial production. Although an amount greater than 0.5 moles does not cause particular problems in conducting the reaction, it may become uneconomical.

It is optional to add a phosphine in the step (b), since it may stabilize the palladium complex compound in some cases to make the reaction proceed preferably. The phosphine may be selected from common phosphines, such as triphenylphosphine, tri-o-tolylphosphine, triethylphosphine, tri-n-butylphosphine, 1,1'-bis(diphenylphosphino)ferrocene (dppf), 1,4-bis(diphenylphosphino)butane, 1,3-bis(diphenylphosphino)propane, and 1,2-bis(diphenylphosphino)ethane. The phosphine used in the step (b) may be in an amount of 10 moles or less, preferably 5 moles or less, more preferably 3 moles or less, per mol of the palladium complex compound. If it is greater than 10 moles, the reaction rate may become too slow. Furthermore, it may become uneconomical. The step (b) can proceed without adding a phosphine. In particular, in case that the after-explained neutral inorganic salt is coexistent with the other reactants, it is possible to obtain a sufficient reaction rate with no addition of phosphine.

A base is essential for the step (b). Its nonlimitative examples are inorganic bases such as potassium acetate, sodium acetate, sodium hydroxide, potassium hydroxide, sodium carbonate, and potassium carbonate; and organic bases such as triethylamine, tripropylamine, tri-n-octylamine, triallylamine, pyridine, and N,N-dimethylaniline. The base may be in an amount of 1–10 moles, preferably 1–5 moles, more preferably 1–3 moles, per mol of the sulfonic ester [4]. If it is less than 1 mole, the reaction may not proceed sufficiently, causing low yield. An amount greater than 10 moles does not increase the yield further and makes the unreacted base remain in the system. This is economically disadvantageous.

The step (b) can be conducted in a solvent or without using any reaction solvent. The solvent may be selected from pentane, hexane, benzene, toluene, xylene, diethyl ether, dioxane, tetrahydrofurane, acetone, methyl isobutyl ketone, acetonitrile, pyridine, N,N-dimethylformamide, N,N-dimethylacetamide, dimethylsulfoxide, and water. In case that the base is in the form of liquid, it serves as a solvent, too. With this, it is possible to obtain an effect similar to the case of adding a solvent.

It is particularly preferable to add a neutral inorganic salt in the step (b), since it enhances the reaction rate and allows the reaction to proceed at a lower temperature with an improved yield. Its nonlimitative examples are potassium fluoride, potassium chloride, potassium bromide, potassium iodide, lithium fluoride, lithium chloride, lithium bromide, and lithium iodide. The neutral inorganic salt may be in an amount of 0.01–10 moles, preferably 0.1–5 moles, more preferably 0.5–2 moles, per mol of the sulfonic ester [4]. If it is less than 0.01 moles, the advantageous effect caused by adding the neutral inorganic salt may be insufficient. An amount greater than 10 moles may not further improve the yield and may become economically disadvantageous.

The reaction of the step (b) can be conducted by charging a reactor with the above-mentioned reagents, then by sealingly closing the reactor, then by introducing carbon monoxide into the reactor, and then by stirring the mixture under normal pressure (e.g., atmospheric pressure) or a pressurized condition. It is optional to make another gas (preferably inert gas such as nitrogen, helium and argon) other than carbon monoxide coexistent with the other reagents. Each of the air and oxygen is not preferable as the another gas, since it may lower the palladium catalytic activity. Normally, it is not necessary to use the another gas. The partial pressure (in terms of absolute pressure) of carbon monoxide is preferably 0.01–10 MPa, more preferably 0.05–1.5 MPa. If it is lower than 0.01 MPa, the reaction may not proceed sufficiently, thereby lowering yield. Even if it is higher than 10 MPa, the yield of the target product may not improve further. Furthermore, it may require the reactor to have an improved strength. As the reaction proceeds in the step (b), carbon monoxide is consumed either under normal pressure or under pressurized condition. Therefore, it is preferable to introduce carbon monoxide intermittently or continuously into the system in order to maintain the carbon monoxide partial pressure at a constant level. The reaction temperature of the step (b) may be in a range of 0–200° C., preferably 0–150° C., more preferably 0–120° C. The optimum reaction temperature may be changed depending on the types and the amounts of the reagents (e.g., palladium complex compound, neutral inorganic salt, and base).

After completing the step (b), the reaction mixture may be subjected to a normal purification procedure. For example, it is possible to add a large excess of water to the reaction mixture, followed by sufficient stirring, extraction with an organic solvent, and removal of the solvent by distillation, thereby obtaining the benzopyrancarboxylic acid [1].

The second process will be described in detail in the following. As stated above, it is possible by the second process to easily synthesize the target product (i.e., the acetophenone [5]) from the alkoxybenzene [6] (starting material). In fact, the present inventors have unexpectedly found that the alkoxybenzene [6] is remarkably higher than 4-(perfluoroalkyl)phenol [8] with respect to (a) chemical stability and (b) reactivity in Friedel-Crafts type electrophilic substitution reactions and that an acylation of the alkoxybenzene [6] proceeds smoothly under a mild condition of 50° C. or lower by reacting the alkoxybenzene [6] with acetic anhydride or an acyl halide in the presence of a Lewis acid, thereby easily synthesizing 2-alkoxy-5-(perfluoroalkyl) acetophenone [7].

The alkoxybenzene [6] can easily be produced by reacting the 4-(perfluoroalkyl)phenol [8] with an alkylation agent or by reacting a 4-(perfluoroalkyl)halogenobenzene [9] with a metal alcoholate.

The reaction scheme from the 4-(perfluoroalkyl)phenol [8] or 4-(perfluoroalkyl)halogenobenzene [9] to the acetophenone [5] can be shown as follows.

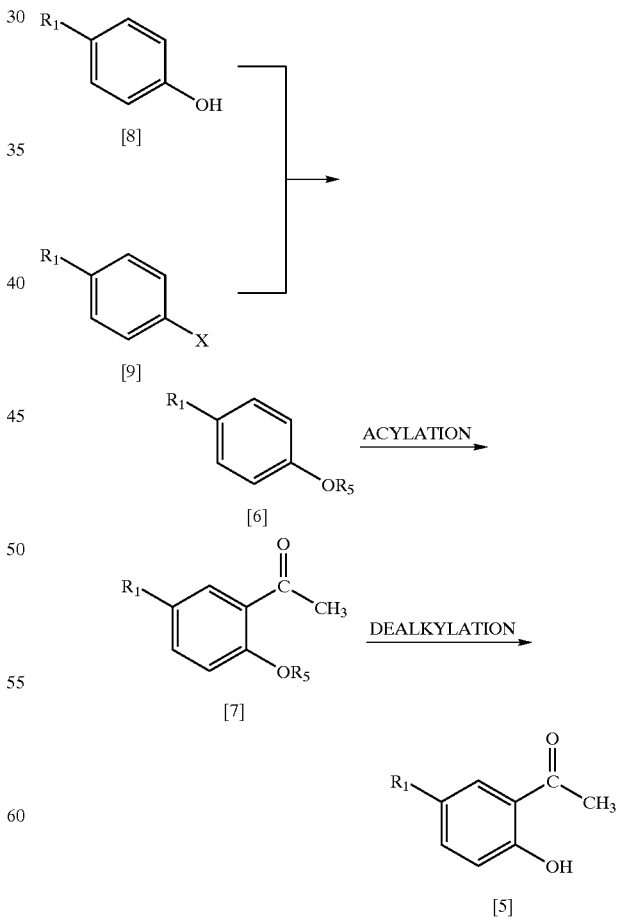

Similar to the first process, the substituent $R_1$ of the general formulas [5] to [9] is a perfluoroalkyl group that is represented by $C_nF_{2n+1}$ where n is an integer of 1–10 and that optionally has a branch in its carbon structure. In view of its availability, n is preferably 1, 2 or 3. In this case, $R_1$ is trifluoromethyl group ($CF_3$), pentafluoroethyl group ($C_2F_5$), heptafluoro-n-propyl group ($CF_3CF_2CF_2$), or heptafluoro-i-propyl group ($CF_3CFCF_3$). Of these, trifluoromethyl group (where n=1) is particularly preferable in view of its availability and usefulness of the target product, 2-hydroxy-5-(trifluoromethyl) acetophenone [5].

$R_5$ of the general formulas [6] and [7] is a straight-chain or non-straight-chain alkyl group having a carbon atom number of 1–20. In view of its availability, $R_5$ is preferably methyl group, ethyl group, n-propyl group or i-propyl group, particularly preferably methyl group.

The intermediate of the second process, 2-methoxy-5-(trifluoromethyl)acetophenone represented by the following formula [10], where $R_1$ is $CF_3$ and $R_5$ is methyl group, is a novel compound.

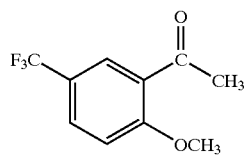

[10]

As stated above, the step (c) can be conducted by reacting the alkoxybenzene [6] with acetic anhydride or an acyl halide in the presence of a Lewis acid, thereby synthesizing the acetophenone [7]. The step (c) will be described in detail in the following.

Although the order of adding the reagents is not particularly limited in the step (c), it is preferable that the alkoxybenzene [6] is mixed with acetic anhydride or an acyl halide, and then the resulting mixture is added intermittently or continuously in a dropwise manner to a reaction vessel containing a Lewis acid (e.g., trifluoromethanesulfonic acid), since this procedure makes it easy to control the reaction temperature.

Although the reagents of the step (c) are not particularly limited in their relative amounts, it is preferable that the acetic anhydride or acyl halide and the Lewis acid are in equimolar amounts or slightly greater relative to that of the alkoxybenzene [6]. For example, it is preferable that the acetic anhydride or acyl halide is in 1.0–3.0 moles and the Lewis acid is in 1.0–10.0 moles relative to 1.0 mol of the alkoxybenzene [6]. If the acetic anhydride or acyl halide and the Lewis acid are in amounts less than their preferable lower limit (i.e., 1.0 mole), yield of the acetophenone [7] may become too low. Even if they are in amounts greater than their preferable upper limits (i.e., 3.0 moles and 10.0 moles), the reaction proceeds. This, however, may become economically disadvantageous.

The Lewis acid used in the step (c) is not limited to particular types. Its preferable examples include trifluoromethanesulfonic acid, hydrofluoric acid anhydride, fuming sulfuric acid, and sulfuric acid. Of these, trifluoromethanesulfonic acid is particularly preferable, since it is in the form of liquid at normal temperature (e.g., room temperature) and thereby easy for handling and since it is high in activity as a Lewis acid. In the step (c), it is not preferable to use aluminum chloride anhydride, which is often used as a catalyst in Friedel-Crafts type electrophilic substitution reactions, since it tends to replace a fluorine atom(s) of a perfluoroalkyl group (e.g., trifluoromethyl group and pentafluoroethyl group) directly bonded to the benzene ring with a chlorine atom(s).

In the step (c), acetic anhydride or an acyl halide (e.g., acetyl fluoride, acetyl chloride, acetyl bromide and acetyl iodide) is used as an acylation agent. Of these, acetic anhydride is particularly preferable, since it is particularly high in reactivity. It is optional to use other aclyation agents and to use a plurality of acylation agents at the same time.

The step (c) is usually conducted in a solvent. However, in case that a Lewis acid (e.g., trifluoromethanesulfonic acid) in the form of liquid is used in the reaction, the Lewis acid serves as a reaction solvent, too. Therefore, there is no need for adding another reaction solvent. The another reaction solvent may be selected from carbon disulfide, dichloromethane, carbon tetrachloride, and 1,2-dichloroethane.

The reaction temperature of the step (c) is not particularly limited. It is preferably 0–50° C., more preferably 0–30° C., from the viewpoint of suppressing the decomposition of the perfluoroalkyl group ($R_1$). Although the time for completing the step (c) may be approximately in a range of 1–12 hrs, it may vary depending on the reaction conditions. Therefore, it is preferable to terminate the reaction after confirming that the alkoxybenzene [6] has been consumed sufficiently by monitoring the progress of the reaction using a conventional analytical technique such as gas chromatography or liquid chromatography.

The purification process after the step (c) is not particularly limited. For example, it is possible to wash the reaction liquid with water to remove salts, aqueous unreacted components and the like, followed by extraction with a non-aqueous organic solvent and then removal of the solvent by distillation, thereby obtaining the alkoxyacetophenone [7].

The step (f) for producing the alkoxybenzene [6] will be described in detail in the following. It is possible to easily produce the alkoxybenzene [6] by the process (a) in which the 4-(perfluoroalkyl)phenol [8] is reacted with an alkylation agent or by the process (b) in which the 4-(perfluoroalkyl) halogenobenzene [9] is reacted with a metal alcoholate (e.g., sodium methoxide).

The process (a) of the step (f) can be conducted by any one of conventional techniques for alkylating hydroxyl group. As a first technique, 4-(perfluoroalkyl)phenol [8] can be reacted with an alkyl sulfate (e.g., dimethyl sulfate and diethyl sulfate), alkyl carbonate (e.g., dimethyl carbonate and diethyl carbonate) or alkyl halide (e.g., methyl chloride) in the presence of a base. As a second technique, it can be reacted with a diazoalkane compound (e.g., diazomethane). As a third technique, it can be reacted with an olefinic compound in the presence of an acid catalyst. Of these techniques, the first technique is particularly preferable, since the raw materials are easily accessible and since the reaction proceed mildly.

It is preferable to conduct the process (a) in a solvent. Although this solvent is not limited to particular types, it is preferable to use a polar solvent to make the reaction proceed mildly. Exemplary polar solvents include acetone, acetonitrile, methanol, ethanol, N,N-dimethylformamide, and nitromethane. Of these, acetone is particularly preferable, since it is chemically stable and thereby easy for handling.

In the first technique of the process (a), it is necessary to add a base in an amount of 1.0–1.5 moles (in the case of a monovalent base such as sodium hydroxide) or 0.5–1.0 mole (in the case of a bivalent base such as potassium carbonate) per mol of the 4-(perfluoroalkyl)phenol [8]. The base is not limited to particular types, and it can be selected from common bases such as sodium carbonate, potassium carbonate, sodium hydroxide, potassium hydroxide, and calcium hydroxide. It is possible to conduct the reaction by adding a base to the 4-(perfluoroalkyl)phenol [8], then by stirring the mixture sufficiently, and then by adding an alkylation agent, followed by stirring. The alkylation agent is in an amount of preferably 0.5–3.0 moles, more preferably 0.5–1.5 moles, per mol of the 4-(perfluoroalkyl)phenol [8], in the case of an alkylation agent having two alkyl groups in the molecule. Although the reaction temperature is not particularly limited, it is preferably 0–100° C., more preferably 10–60° C., throughout the process (a). In order to properly control the reaction temperature, it is preferable to mix the reagents intermittently or continuously.

In the process (a), the period of time required from completion of mixing all the reagents until completion of the reaction may be approximately 2–6 hrs. However, it may vary depending on the reaction conditions. Therefore, it is preferable to conduct the reaction, while monitoring its progress by a common analytical technique such as gas chromatography.

The process (b) of the step (f) can be conducted by adding in a polar solvent (e.g., methanol and ethanol) a metal alcoholate (e.g., sodium methoxide, lithium methoxide, sodium ethoxide, and lithium ethoxide) in an amount preferably 1–10 parts by mole, more preferably 1–5 parts by mole, to 1 part by mole of the halogenobenzene [9], followed by heating and stirring. The reaction temperature of the process (b) is preferably 80–200° C., more preferably 120–180° C. If it is higher than boiling point of the solvent, it is necessary to conduct the reaction in a pressure-proof reaction vessel in a tightly sealed condition. Although the time required for the reaction may be about 3–10 hrs, it may vary depending on the reaction conditions. Therefore, it is preferable to conduct the reaction, while monitoring the progress of the reaction using gas chromatography or liquid chromatography.

In each of the processes (a) and (b), the reaction mixture obtained by completing the reaction may be subjected to a normal purification procedure of organic syntheses, thereby separating the alkoxybenzene [6]. For example, the reaction mixture can be distilled by an evaporator to remove the solvent, followed by washing sufficiently with water, then extraction with a nonaqueous organic solvent, then removal of the solvent by distillation, and then distillation of the residue, thereby obtaining the alkoxybenzene [6].

The step (d) of dealkylating the acetophenone [7] by a dealkylating agent to obtain the acetophenone [5] will be described in detail in the following.

The reaction of the step (d) can be conducted by mixing together the acetophenone [7] and a dealkylating agent and then by stirring the mixture. The dealkylating agent is not particularly limited with respect to its type and operational procedure, and it may be selected from generally known dealkylating agents such as concentrated sulfuric acid, concentrated hydrochloric acid, concentrated nitric acid, hydrobromic acid (HBr) aqueous solution, hydroiodic acid (HI) aqueous solution, boron tribromide ($BBr_3$), and boron trichloride ($BCl_3$), and sodium hydroxide.

In some cases, the dealkylation of the step (d) may not proceed sufficiently even if the acetophenone [7] is reacted with a dealkylating agent. In contrast, a drastic heating for accelerating the dealkylation may generate undesirable side reactions (e.g., decomposition of perfluoroalkyl group). Thus, the present inventors eagerly examined the solution of such problems of the dealkylation. As a result, the present inventors unexpectedly found that the above-mentioned problems can be solved by.any one of the following three methods.

The first method is that the alkoxyacetophenone [7] is reacted with boron tribromide ($BBr_3$). It is preferable to conduct this reaction in a solvent. Although this solvent is not limited to particular types, methylene chloride is particularly preferable since it allows the reaction to proceed smoothly. It is preferable to conduct the reaction at −50° C. or lower under nitrogen gas flow, more preferably at −78° C. or lower under nitrogen gas flow. For the purpose of keeping the reaction conditions constant, it is preferable to conduct the first method by separately dissolving the alkoxyacetophenone [7] and boron tribromide in methylene chloride to prepare two solutions, then by gradually adding one of these solutions in a dropwise manner to the other solution while stirring the other solution, and then by continuing stirring under the same condition. Although the stirring time may be about 1–5 hrs, it may deviate therefrom depending on the reaction conditions. In the first method, boron tribromide is in an amount preferably 0.33–2.0 moles relative to 1 mol of the alkoxyacetophenone [7].

The second method of the step (d) is that the alkoxyacetophenone [7] is reacted with sodium iodide and trimethylsilylchloride in a solvent. Although this solvent is not limited to particular types, it is preferable to use acetonitrile since it allows the reaction to proceed mildly. It is preferable to conduct the second method by dissolving the alkoxyacetophenone [7] and sodium iodide in a solvent, then by adding trimethylsilylchloride in a dropwise manner to the mixture, and then continuing stirring of the mixture. Although the reagents of the second method are not particularly limited in their relative amounts, it is preferable that each of sodium iodide and trimethylsilylchloride is in a range of 1.0–3.0 moles per mol of the alkoxyacetophenone [7]. The reaction temperature is not particularly limited. The temperature, at which the reagents are mixed together, is preferably 10–40° C. The temperature for the subsequent stirring is preferably the reflux temperature of acetonitrile if acetonitrile is used as the solvent. The period of time required for such refluxing (heating) may be about 5–70 hrs, but it may deviate therefrom depending on the reaction conditions.

The third method of the step (d) is conducted by dissolving a strong base, such as a metal hydride (e.g., sodium hydride) or a metal alkoxide (e.g., sodium methoxide), in a solvent to prepare a first solution, then by adding a thiol (e.g., ethanethiol and 1-octanethiol) to the first solution to prepare a second solution (a solution of a metal salt of thiol), then by adding the alkoxyacetophenone [7] to the second solution, and then by continuing stirring of the resulting solution. Although the solvent of the third method is not limited to particular types, it is particularly preferable to use N,N-dimethylformamide since it allows the reaction to proceed mildly. The reaction temperature is not particularly limited. The temperature, at which the second solution is prepared, is preferably 0–30° C. The temperature, at which the alkoxyacetophenone [7] is added to the second solution and then the stirring is conducted, is preferably 0–100° C. Although the period of time for the stirring may be 15 minutes to 2 hrs, it may deviate therefrom depending on the reaction conditions. Although the reagents of the third method are not particularly limited in their relative amounts, it is preferable that each of the strong base and the thiol is in an equimolar amount or greater relative to that of the alkoxyacetophenone [7]. For example, each of them is preferably in 1.0–1.1 moles relative to 1.0 mole of the alkoxyacetophenone [7] in terms of reactivity and economy.

In each of the first to third methods of the step (d), it is preferable to conduct the reaction, while monitoring the progress of the reaction by using a normal analytical technique such as gas chromatography and liquid chromatography. It is possible to terminate the reaction after confirming that the alkoxyacetophenone [7] has sufficiently been consumed.

The reaction mixture obtained by the step (d) may be subjected to a normal post-treatment. For example, the reaction mixture is sufficiently washed with water, followed by extraction with a nonaqueous organic solvent and then removal of this solvent by distillation, thereby obtaining the target product, the hydroxyacetophenone [5].

The following nonlimitative Examples are illustrative of the present invention.

EXAMPLE 1

SYNTHESIS OF 2,2-BIS(FLUOROMETHYL)-3,4-DIHYDRO-6-(TRIFLUOROMETHYL)-2 H-1-BENZOPYRAN-4-ONE

A three-necked 50-ml flask (equipped with a thermometer, a reflux condenser and a dropping funnel) was charged with 2.2 g (10.8 mmol) of 5-trifluoromethyl-2-hydroxyacetophenone, 2.2 g (23.4 mmol) of 1,3-difluoroacetone, and 40 ml of methanol. Then, 2.0 g (28.1 mmol) of pyrrolidine were added in a dropwise manner by spending 5 minutes to the mixture at a temperature of 30–34° C. with stirring of the mixture. Then, the mixture was heated under reflux for 6 hrs, followed by distilling methanol off, then by adding a 2 mol/liter hydrochloric acid to make the reaction mixture acid, and then by extraction two times with 30 ml of ethyl acetate. The resulting two ethyl acetate extracts were combined together, followed by washing with water, then by drying with magnesium sulfate anhydride, and then by filtration. Then, the ethyl acetate was distilled off by an evaporator. The resulting residue was purified by silica gel column chromatography (developing liquid: ethyl acetate/n-hexane=⅕), thereby obtaining 1.1 g (3.9 mmol) of 2,2-bis(fluoromethyl)-3,4-dihydro-6-(trifluoromethyl) -2H- 1- benzopyran-4-one (yield: 36%). This product was found to have the following properties.

Melting point: 73.0–74.5° C.

$^1$H-NMR (standard substance: TMS; solvent: $CDCl_3$)σ (ppm): 2.98 (s, 2 H), 4.61 (dd, J=47.6, 2.4 Hz, 4 H), 7.15 (d, J=8.8 Hz, 1 H), 7.76 (dd, J=8.8, 2.4 Hz, 1 H), 8.17 (d, J=2.4 Hz, 1 H) $^{19}$F-NMR (standard substance: $CCl_3F$; solvent: $CDCl_3$)σ (ppm): −62.81 (s, 3 F), −232.40 (t, J=47.6 Hz, 2 F)

EXAMPLE 2

SYNTHESIS OF 2,2-BIS(FLUOROMETHYL)-3,4-DIHYDRO-6-(TRIFLUOROMETHYL) -2 H-1-BENZOPYRAN-4-ONE

A three-necked 200-ml flask (equipped with a thermometer, a reflux condenser and a dropping funnel) was charged with 10.0 g (49.0 mmol) of 5-trifluoromethyl-2-hydroxyacetophenone, 5.53 g (58.8 mmol) of 1,3-difluoroacetone, and 150 ml of methanol. Then, 4.9 ml (58.8 mmol) of pyrrolidine were added in a dropwise manner by spending 10 minutes to the mixture under cooling with ice, while the mixture was stirred. Then, the mixture was stirred at room temperature for 1 hr and then heated under reflux for 5 hrs, followed by distilling methanol off, then by adding a 2 mol/liter hydrochloric acid to make the reaction mixture acid, and then by extraction two times with 150 ml of metyl tertiary butyl ether (MTBE). The resulting two MTBE extracts were combined together, followed by washing with 60 ml of a 2 mol/L sodium hydroxide aqueous solution and then with water, then by drying with 5 g of magnesium sulfate anhydride, and then by filtration. Then, the MTBE was distilled off by an evaporator. The resulting residue was purified by recrystallization using a solvent (i.e., MTBE/n-hexane=⅓), thereby obtaining 7.06 g (25.2 mmol) of 2,2-bis(fluoromethyl)- 3,4-dihydro-6-(trifluoromethyl)-2 H-1-benzopyran-4-one (yield: 51.4%).

EXAMPLE 3

SYNTHESIS OF TRIFLUOROMETHANESULFONIC ACID 2,2-BIS(FLUOROMETHYL)-6-(TRIFLUOROMETHYL)-2 H- 1 -BENZOPYRAN-4-YL ESTER

A three-necked 50 -ml flask (equipped with a thermometer and a dropping funnel) was charged with 1.0 g (3.6 mmol) of 2,2-bis(fluoromethyl)- 3,4-dihydro-6-(trifluoromethyl)-2 H- 1-benzopyran-4-one, 1.8 g (8.9 mmol) of 2,6-di-tert-butyl-4-methylpyridine, and 10 ml of methylene chloride. Then, 2.0 g (7.0 mmol) of trifluoromethanesulfonic acid anhydride were added in a dropwise manner by spending 5 minutes to the mixture under cooling in an iced water bath at 5–10° C., while the mixture was stirred. After completing the dropping, the temperature of the mixture was gradually increased to room temperature, followed by stirring for 140 hr at room temperature. Then, the methylene chloride was distilled off by an evaporator. The resulting residue was purified by silica gel column chromatography (developing liquid: ethyl acetate/n-hexane=⅛), thereby obtaining 1.1 g (2.7 mmol) of trifluoromethanesulfonic acid 2,2-bis(fluoromethyl) -6-(trifluoromethyl)- 2 H- 1-benzopyran-4-yl ester (yield: 75%). This product was found to have the following properties.

$^1$H-NMR (standard substance: TMS; solvent: $CDCl_3$)σ (ppm): 4.51–4.73 (m, J=46.4 Hz, 4 H), 5.78 (s, 1 H), 7.04 (d, J=8.8 Hz, 1 H), 7.53 (d, J=2.0 Hz, 1 H), 7.58 (dd, J=8.8, 2.0 Hz, 1 H) $^{19}$F-NMR (standard substance: $CCl_3F$; solvent: $CDCl_3$)σ (ppm): −62.85 (s, 3 F), −73.51 (s, 3 F), −232.91 (t, J=46.4 Hz, 2 F)

EXAMPLE 4

SYNTHESIS OF TRIFLUOROMETHANESULFONIC ACID 2,2-BIS(FLUOROMETHYL)- 6-(TRIFLUOROMETHYL)-2 H- 1-BENZOPYRAN-4-YL ESTER

A three-necked 200-ml flask (equipped with a thermometer and a dropping funnel) was charged with 10.77 g (38.5 mmol) of 2,2-bis(fluoromethyl)- 3,4-dihydro-6-(trifluoromethyl)-2 H-1-benzopyran-4-one, 11.7 g (96.1 mmol) of 4-dimethylaminopyridine (DMAP), and 96 ml of methylene chloride. Then, 26.4 g (93.6 mmol) of trifluoromethanesulfonic acid anhydride were added in a dropwise manner by spending 5 minutes to the mixture under cooling in an iced water bath at 5–10° C., while the mixture was stirred. After completing the dropping, the temperature of the mixture was gradually increased to room temperature, followed by stirring for 18 hr at room temperature. The resulting reaction liquid was filtered, followed by washing two times with water. Then, the methylene chloride was distilled off by an evaporator. The resulting residue was dissolved in 50 ml of hexane, followed by filtration. The resulting filtrate was washed with 12 ml of 3 mol/L (14%) ammonium chloride aqueous solution, then concentrated with hexane, and then purified by silica gel short column chromatography (developing liquid: MTBE/n-hexane=1/10), thereby obtaining 12.53 g (30.41 mmol) of trifluoromethanesulfonic acid 2,2-bis(fluoromethyl)-6-(trifluoromethyl)-2 H-1-benzopyran-4-yl ester (yield: 79.1%).

EXAMPLE 5

SYNTHESIS OF 2,2-BIS(FLUOROMETHYL)-6-(TRIFLUOROMETHYL)-2 H- 1 -BENZOPYRAN-4-CARBOXYLIC ACID

A three-necked 50-ml flask (equipped with a reflux condenser, a thermometer, and a CO introducing pipe connected with a balloon charged with carbon monoxide gas) was charged with 1.0 g (2.4 mmol) of trifluoromethanesulfonic acid 2,2-bis(fluoromethyl)-6- (trifluoromethyl)-2H-1-benzopyran-4-yl ester, 0.95 g (9.7 mmol) of potassium acetate, 0.4 g (2.4 mmol) of potassium iodide, and 10 ml of N,N-dimethylacetoamide. While the mixture was stirred, a mixture of 6 mg (0.027 mmol) of palladium acetate, 14 mg (0.053 mmol) of triphenylphosphine, and 2 ml of N,N-dimethylacetoamide was added. Under normal pressure, the mixture was stirred at 120° C. for 1 hr, while maintaining carbon monoxide atmosphere.

After the reaction, the reaction liquid was poured into 50 ml of 2 mol/L hydrochloric acid, followed by shaking for 5 min and then extraction two times with 50 ml of ether. The resulting two ether extracts were combined together, followed by washing with water, then by drying with 5 g of magnesium sulfate anhydride, and then by filtration. Then, the ether was distilled off by an evaporator. The resulting residue was dissolved in 50 ml of a saturated sodium hydrogencarbonate aqueous solution, followed by washing with 5 ml of methylene chloride. The resulting aqueous layer was made acid by concentrated hydrochloric acid, followed by extraction two times with 50 ml of ethyl acetate. The resulting two ethyl acetate extracts were combined together, followed by washing with water, then by drying with 5 g of magnesium sulfate anhydride, and then by filtration. Then, the ethyl acetate was distilled off by an evaporator, thereby obtaining 0.3 g (0.97 mmol) of 2,2-bis(fluoromethyl)-6-(trifluoromethyl)-2 H-1-benzopyran-4-carboxylic acid (yield: 40.1%). This product was found to have the following properties.

Melting point: 159–161° C.

$^1$H-NMR (standard substance: TMS; solvent: $CDCl_3$)$\sigma$ (ppm): 4.52–4.74 (m, J=46.4 Hz, 4 H), 6.95 (s, 1 H), 7.04 (d, J=8.4 Hz, 1 H), 7.52 (dd, J=8.4, 2.0 Hz, 1 H), 8.36 (d, J=2.0 Hz, 1 H), 10.0–10.4 (1 H, bs)

$^{19}$F-NMR (standard substance: $CCl_3F$; solvent: $CDCl_3$)$\sigma$ (ppm): −62.48 (s, 3 F), −233.97 (t, J=46.4 Hz, 2 F)

EXAMPLE 6

SYNTHESIS OF 2,2-BIS(FLUOROMETHYL)-6-(TRIFLUOROMETHYL)-2 H-1-BENZOPYRAN-4-CARBOXYLIC ACID

A three-necked 50-ml flask (equipped with a reflux condenser, a thermometer, and a CO introducing pipe connected with a balloon charged with carbon monoxide gas) was charged with 2.00 g (4.85 mmol) of trifluoromethanesulfonic acid 2,2-bis(fluoromethyl)-6- (trifluoromethyl)-2 H-1-benzopyran-4-yl ester, 1.90 g (19.4 mmol) of potassium acetate, 206 mg (4.85 mmol) of lithium chloride, and 25 ml of N,N-dimethylformamide. Under stirring of the mixture, 50 mg (0.0485 mmol) of tris(dibenzylidene)(chloroform) dipalladium ($Pd_2(dba)_3(CHCl3)$) were added. Under normal pressure, the reaction was conducted at 25° C. for 2 hr, while maintaining carbon monoxide atmosphere. After the reaction, the reaction liquid was poured into 50 ml of 2 mol/L sodium hydroxide aqueous solution, followed by shaking for 20 min, then adding concentrated hydrochloric acid to make it acid, and then extraction two times with 50 ml of MTBE. The resulting two MTBE extracts were combined together, followed by washing with water, then by drying with 5 g of magnesium sulfate anhydride, and then by filtration. Then, the MTBE was distilled off by an evaporator. The resulting residue was dissolved in 50 ml of a saturated sodium hydrogencarbonate aqueous solution, followed by washing with 5 ml of methylene chloride. The resulting aqueous layer was made acid by concentrated hydrochloric acid, followed by extraction two times with 50 ml of MTBE. The resulting two MTBE extracts were combined together, followed by washing with water, then by drying with 5 g of magnesium sulfate anhydride, and then by filtration. Then, the MTBE was distilled off by an evaporator, thereby obtaining 1.30 g (4.22 mmol) of 2,2-bis(fluoromethyl)-6-(trifluoromethyl)-2 H-1- benzopyran-4-carboxylic acid (yield: 87.0%).

EXAMPLE 7

SYNTHESIS OF 2,2-BIS(FLUOROMETHYL)-6-(TRIFLUOROMETHYL)-2 H- 1-BENZOPYRAN-4-CARBOXYLIC ACID

A three-necked 200 -ml flask (equipped with a reflux condenser, a thermometer, and a CO introducing pipe connected with a balloon charged with carbon monoxide gas) was charged with 6.00 g (14.6 mmol) of trifluoromethanesulfonic acid 2,2-bis(fluoromethyl)-6-(trifluoromethyl)-2 H-1 -benzopyran-4-yl ester, 5.7 g (58.2 mmol) of potassium acetate, 618 mg (14.6 mmol) of lithium chloride, and 75 ml of N,N-dimethylformamide. Under stirring of the mixture, 15 mg (0.0146 mmol) of tris(dibenzylidene) (chloroform) dipalladium ($Pd_2(dba)_3(CHCl_3)$) were added. Under normal pressure, the reaction was conducted at 25° C. for 2 hr, while maintaining carbon monoxide atmosphere. After the reaction, the reaction liquid was poured into 150 ml of 2 mol/L sodium hydroxide aqueous solution, followed by shaking for 20 min, then adding concentrated hydrochloric acid to make it acid, and then extraction two times with 150 ml of MTBE. The resulting two MTBE extracts were combined together, followed by washing with water, then by drying with 15 g of magnesium sulfate anhydride, and then by filtration. Then, the MTBE was distilled off by an evaporator. The resulting residue was dissolved in 150 ml of a saturated sodium hydrogencarbonate aqueous solution, followed by washing with 15 ml of methylene chloride. The resulting aqueous layer was made acid by concentrated hydrochloric acid, followed by extraction two times with 150 ml of MTBE. The resulting two MTBE extracts were combined together, followed by washing with water, then by drying with 15 g of magnesium sulfate anhydride, and then by filtration. Then, the MTBE was distilled off with an evaporator, thereby obtaining 3.41 g (11.1 mmol) of 2,2-bis(fluoromethyl)- 6-(trifluoromethyl)-2 H- 1-benzopyran-4-carboxylic acid (yield: 76%).

EXAMPLES 8-1 TO 8-5 SYNTHESIS OF 2,2-BIS(FLUOROMETHYL)-6-(TRIFLUOROMETHYL)-2 H- 1-BENZOPYRAN-4-CARBOXYLIC ACID

A three-necked 50-ml flask (equipped with a reflux condenser, a thermometer, and a CO introducing pipe connected with a balloon charged with carbon monoxide gas) was charged with 1.0 g (2.4 mmol) of trifluoromethanesulfonic acid 2,2-bis(fluoromethyl)-6-(trifluoromethyl) -2 H- 1-benzopyran-4-yl ester, 0.95 g (9.7 mmol) of potassium acetate, and 10 ml of N,N-dimethylacetamide. Under stirring of the mixture, predetermined amounts of reagents were added, as shown in Table. Then, the reaction was conducted under conditions shown in Table. After that, the reaction mixture was subjected to the same post-treatments as those of Example 5. As a result, 2,2-bis(fluoromethyl)-6-(trifluoromethyl)-2 H- 1-benzopyran-4-carboxylic acid was obtained, as shown by yield in Table.

was washed two times with 50 ml of water. The obtained n-hexane layer was dried with magnesium sulfate anhydride, followed by concentration by an evaporator and then by removal of hexane by distillation under reduced pressure, thereby obtaining 22.8 g (0.13 moles) of oily 4-(trifluoromethyl)anisole (isolation yield: 84.0%). This product was found to have the following properties.

Melting point: 168° C.

$^1$H-NMR (standard substance: TMS; solvent: $CDCl_3$)σ (ppm): 3.84 (s, 3 H), 6.95 (d, J=8.4 Hz, 2 H), 7.54 (d, J=8.4 Hz, 2 H) $^{19}$F-NMR (standard substance: $CCl_3F$; solvent: $CDCl_3$)σ (ppm): −61.94 (s, 3 F)

EXAMPLE 10

PRODUCTION OF 4-(TRIFLUOROMETHYL)ANISOLE 200 g (1.11mol) of 4-(trifluoromethyl)chlorobenzene, 179 g (3.31 mol) of sodium methoxide, and 600 ml of methanol

TABLE

|  | Ex. 8-1 | Ex. 8-2 | Ex. 8-3 | Ex. 8-4 | Ex. 8-5 |
|---|---|---|---|---|---|
| Reactants |  |  |  |  |  |
| Palladium Complex Compound | Pd(dba)$_2$, 0.024 mmol | Pd$_2$(dba)$_2$. CHCl$_3$, 0.024 mmol | Pd$_2$(dba)$_2$. CHCl$_3$, 0.012 mmol | Pd(OCOMe)$_2$ 0.024 mmol | Pd(OCOMe)$_2$ 0.024 mmol |
| Phosphine Compound | — | — | — | Triphenylphosphine, 0.048 mmol | Triphenylphosphine, 0.048 mmol |
| Neutral Inorganic Salt | — | — | LiCl, 2.4 mmol | — | KI, 2.4 mmol |
| Reaction Conditions |  |  |  |  |  |
| Temp. (° C.) | 25 | 25 | 25 | 50 | 50 |
| Time (hr) | 5 | 1 | 1 | 3 | 5 |
| Yield | 0.96 mmol, 40% | 1.51 mmol, 63% | 2.02 mmol, 84% | 0.60 mmol, 25% | 1.27 mmol, 53% |

Pd(dba)$_2$: bis(dibenzylideneacetone)palladium;
Pd$_2$(dba)$_2$.CHCl$_3$: tris(dibenzylidene) (chloroform) dipalladium;
Pd(OCOMe)$_2$: palladium acetatate

EXAMPLE 9

PRODUCTION OF 4-(TRIFLUOROMETHYL)ANISOLE 25.0 g (0.15 moles) of 4-(trifluoromethyl)phenol and 23.5 g (0.17 moles) of potassium carbonate were mixed in 80 ml of acetone in a 200 ml three-necked flask. The flask was equipped with a reflux condenser, a dropping funnel and a thermometer and was connected with a calcium chloride tube for shielding the flask against moisture of the outside. After the mixing, 21.4 g (0.17 moles) of dimethyl sulfate were added at a temperature of not higher than 30° C. in a dropwise manner to the mixture under stirring. After that, the reaction mixture was refluxed at reflux temperature of acetone for 5 hrs. After completing the reaction, the reaction liquid was cooled down to room temperature. The resulting precipitates (solid) were separated by filtration. The obtained filtrate was concentrated by an evaporator. To the resulting residue 100 ml of water and 100 ml of n-hexane were added, thereby extracting the target product into the n-hexane layer. To the resulting water layer 50 ml of n-hexane were added, thereby conducting an extraction again. The resulting two n-hexane layers were combined together, followed by washing with 80 ml of 2 mol/L sodium hydroxide aqueous solution. The resulting n-hexane layer were mixed together in a pressurized reaction vessel, followed by stirring for 6 hr at 150° C. under tight sealing. The resulting reaction mixture was filtered to remove precipitates. Water was added to the obtained filtrate, followed by extraction with n-hexane. The resulting organic layer was washed with water, followed by drying with magnesium sulfate anhydride and removal of the solvent by distillation. The obtained residue was purified by distillation, thereby obtaining 112 g (0.636 mol) of 4-(trifluoromethyl)anisole (yield: 57%).

EXAMPLE 11

PRODUCTION OF 4-(TRIFLUOROMETHYL)ANISOLE 100 g (0.445 mol) of 4-(trifluoromethyl)bromobenzene, 120 g (2.22 mol) of sodium methoxide, and 300 ml of methanol were mixed together in a pressurized reaction vessel, followed by stirring for 6 hr at 150° C. under tight sealing. The resulting reaction mixture was poured into water, followed by extraction with n-hexane. The resulting organic layer was washed with water, followed by drying with magnesium sulfate anhydride and removal of the solvent by distillation. The obtained residue was purified by distillation, thereby obtaining 49 g (0.278 mol) of 4-(trifluoromethyl)anisole (yield: 62.6%).

EXAMPLE 12

PRODUCTION OF 2-METHOXY-5-(TRIFLUOROMETHYL)ACETOPHENONE 97.0 g (0.65 moles) of trifluoromethanesulfonic acid were put into a 200 ml three-necked flask. The flask was equipped with a reflux condenser, a dropping funnel and a thermometer and was connected with a calcium chloride tube for shielding the flask against moisture of the outside. A mixture of 22.8 g (0.13 moles) of 4-(trifluoromethyl)anisole and 26.5 g (0.26 moles) of acetic anhydride was added in a dropwise manner at a temperature of not higher than 30° C. to the flask under stirring. After the adding, the reaction was conducted for 3 hrs at 20–25° C. The resulting reaction liquid was poured into 300 ml of iced water. Then, 200 ml of ether were added to extract the reaction product. Then, 100 ml of ether were added to the aqueous layer to extract the reaction product again. The resulting two ether layers were combined together, followed by washing with 10% sodium hydrogencarbonate aqueous solution until the ether layer is made basic. The obtained ether layer was washed three times with 100 ml of water, followed by drying with magnesium sulfate anhydride and then concentration by an evaporator, thereby obtaining 20.9 g (0.096 moles) of oily 2-methoxy-5-(trifluoromethyl) acetophe none (isolation yield: 74.0%). This product was found to have the following properties.

$^1$H-NMR (standard substance: TMS; solvent: CDCl$_3$)σ (ppm): 2.63 (s, 3 H), 2.16 (s, 3 H), 7.06 (d, J=8.8 Hz, 1 H), 7.71 (dd, J=8.8, 2.0 Hz, 1 H), 8.06 (d, J=2 Hz, 1 H) $^{19}$F-NMR (standard substance: CCl$_3$F; solvent: CDCl$_3$)σ (ppm): –62.31 (s, 3 F)

EXAMPLE 13

PRODUCTION OF 2-HYDROXY-5-(TRIFLUOROMETHYL)ACETOPHENONE

A 100 ml three-necked flask (equipped with a dropping funnel and a thermometer and connected with a calcium chloride tube for shielding the flask against moisture of the outside) was charged with 5.87 g (0.027 moles) of 2-methoxy-5-(trifluoromethyl)acetophenone and 20 ml of methylene chloride. Then, 27 ml (0.027 moles) of a methylene chloride solution (containing 1.0 mol of boron tribromide per liter of methylene chloride) were added in a dropwise manner at a temperature of not higher than –50° C. under nitrogen gas flow under stirring to the flask in a dry ice and acetone bath. After the adding, the reaction was conducted at about –78° C. for 1 hr. Then, the reaction liquid was poured into 100 ml of iced water. The resulting water layer was extracted with 50 ml of methylene chloride. The obtained methylene chloride layers were combined together, followed by extraction three times with 50 ml of 10% sodium hydroxide aqueous solution. The obtained aqueous layers were combined together, followed by addition of concentrated hydrochloric acid to make the aqueous layer acid and then extraction two times with 100 ml of ether. The obtained ether layer was dried with magnesium sulfate anhydride, followed by concentration by an evaporator, thereby obtaining 1.7 g (0.0083 moles) of oily 2-hydroxy-5-(trifluoromethyl)acetophenone (isolation purity: 30.9%). This product was found to have the following properties.

Melting point: 79° C./800 Pa $^1$H-NMR (standard substance: TMS; solvent: CDCl$_3$)σ (ppm): 2.69 (s, 3 H), 7.07 (d, J=8.8 Hz, 1 H), 7.69 (dd, J=8.8, 2.0 Hz, 1 H), 7.99 (d, J=2.0 Hz, 1 H), 12.55 (s, 1 H) $^{19}$F-NMR (standard substance: CCl$_3$F; solvent: CDCl$_3$)σ (ppm): –62.31 (s, 3 F)

EXAMPLE 14

PRODUCTION OF 2-HYDROXY-5-(TRIFLUOROMETHYL)ACETOPHENONE

A 300 ml three-necked flask (equipped with a reflux condenser, a dropping funnel and a thermometer and connected with a calcium chloride tube for shielding the flask against moisture of the outside) was charged with 20.9 g (0.096 moles) of 2-methoxy- 5-(trifluoromethyl) acetophenone, 28.7 g (0.19 moles) of sodium iodide, and 200 ml of acetonitrile. Under stirring, 20.8 g (0.19 moles) of trimethylsilylchloride were added in a dropwise manner to the flask kept in an iced water bath at a temperature of not higher than 20° C. After the addition, the reaction liquid was refluxed for 40 hr at reflux temperature of acetonitrile. After that, the reaction liquid was cooled down to room temperature, followed by addition of 80 ml of 2 mol/L hydrochloric acid and 200 ml of ether to extract the reaction product. Then, 100 ml of ether were added to the aqueous layer to conduct the extraction again. The obtained ether layers were combined together, followed by washing with saturated sodium thiosulfate aqueous solution to remove iodine and then by extraction three times with 80 ml of 10% sodium hydroxide aqueous solution and then two times with 50 ml of water. The obtained aqueous layers were combined together, followed by addition of concentrated hydrochloric acid to make the aqueous layer acid and then extraction two times with 150 ml of ether. The obtained ether layer was dried with magnesium sulfate anhydride, followed by concentration by an evaporator, thereby obtaining 9.5 g (0.047 moles) of oily 2-hydroxy-5-(trifluoromethyl)acetophenone (isolation purity: 48.6%).

EXAMPLE 15

PRODUCTION OF 2-HYDROXY-5-(TRIFLUOROMETHYL)ACETOPHENONE

A 300 ml three-necked flask (equipped with a reflux condenser, a dropping funnel and a thermometer and connected with a calcium chloride tube for shielding the flask against moisture of the outside) was charged with 5.8 g (0.145 moles) of 60% sodium hydride and 150 ml of dimethylformamide. Then, under stirring, 9.0 g (0.145 moles) of ethanethiol were added under nitrogen gas flow in a dropwise manner by spending 10 min to the flask kept in an ice bath, followed by stirring for 30 min. Then, 30.0 g (0.138 moles) of 2-methoxy-5-(trifluoromethyl) acetophenone were added, and then the resulting reaction liquid was heated at 100° C. Under this condition, the reaction was conducted for 30 min. The resulting reaction mixture was poured into 200 ml of iced water, followed by addition of 300 ml of hexane to extract the reaction product. To the obtained hexane layer 200 ml of 10% sodium hydroxide aqueous were added for the extraction, followed by addition of concentrated hydrochloric acid to make the aqueous layer acid and then extraction two times with 400 ml of hexane. The obtained hexane layer was dried with magnesium sulfate anhydride, followed by concentration by an evaporator and then distillation under reduced pressure, thereby obtaining 19.5 g (0.096 moles) of 2-hydroxy-5-(trifluoromethyl) acetophenone (isolation purity: 69.5%).

The entire contents of Japanese Patent Application No. 2001-300314 (filed Sep. 28, 2001) and 2001-332471 (filed Oct. 30, 2001), of which priorities are claimed in the present application, are incorporated herein by reference.

What is claimed is:

1. A process for producing a 2,2-bis(fluoromethyl)-6-(perfluoroalkyl)-2H-1-benzopyran-4-carboxylic acid represented by the general formula [1], the process comprising the steps of:
   (a) reacting a 2,2-bis(fluoromethyl)-6-(perfluoroalkyl)-2 H-1-benzopyran-4-one, represented by the general formula [2], with a perfluoroalkanesulfonic acid anhydride, represented by the general formula [3], in the presence of a base, thereby obtaining a perfluoroalkanesulfonic 2,2-bis(fluoromethyl)-6-(perfluoroalkyl)-2 H-1-benzopyran-4-yl ester represented by the general formula [4]; and
   (b) reacting the benzopyranyl ester with carbon monoxide in the presence of a palladium complex compound and a base, thereby obtaining the carboxylic acid,

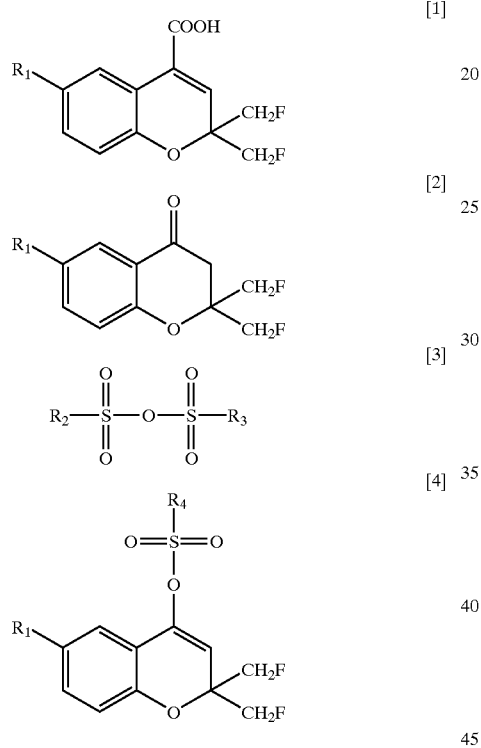

where $R_1$ is a perfluoroalkyl group that is represented by $C_nF_{2n+1}$ where n is an integer of 1–10 and that optionally has a branch in a carbon structure of the perfluoroalkyl group;
each of $R_2$ and $R_3$ is independently a lower perfluoroalkyl group that is represented by $C_nF_{2n+1}$ where n is an integer of 1–10 and that optionally has a branch in a carbon structure of the lower perfluoroalkyl group; and
$R_4$ is identical with the $R_2$ or $R_3$.

2. A process for producing a 2,2-bis(fluoromethyl)-6-(perfluoroalkyl)-2 H-1-benzopyran-4-carboxylic acid represented by the general formula [1], the process comprising the steps of:
   (c) reacting a 4-(perfluoroalkyl)alkoxybenzene, represented by the general formula [6], with acetic anhydride or an acyl halide in the presence of a Lewis acid, thereby obtaining a 2-alkoxy-5-(perfluoroalkyl) acetophenone represented by the general formula [7];
   (d) dealkylating the 2-alkoxy-5-(perfluoroalkyl) acetophenone by a dealkylating agent, thereby obtaining a 2-hydroxy-5-(perfluoroalkyl)acetophenone represented by the general formula [5];
   (e) reacting the 2-hydroxy-5-(perfluoroalkyl) acetophenone with 1,3-difluoroacetone in the presence of a base, thereby obtaining a 2,2-bis(fluoromethyl)-6-(perfluoroalkyl)-2H-1-benzopyran-4-one represented by the general formula [2];
   (a) reacting the 2,2-bis(fluoromethyl)-6-(perfluoroalkyl)-2H-1-benzopyran-4-one with a perfluoroalkanesulfonic acid anhydride, represented by the general formula [3], in the presence of a base, thereby obtaining a perfluoroalkanesulfonic 2,2-bis(fluoromethyl)-6-(perfluoroalkyl)-2H- 1-benzopyran-4-yl ester represented by the general formula [4]; and
   (b) reacting the benzopyranyl ester with carbon monoxide in the presence of a palladium complex compound and a base, thereby obtaining the carboxylic acid,

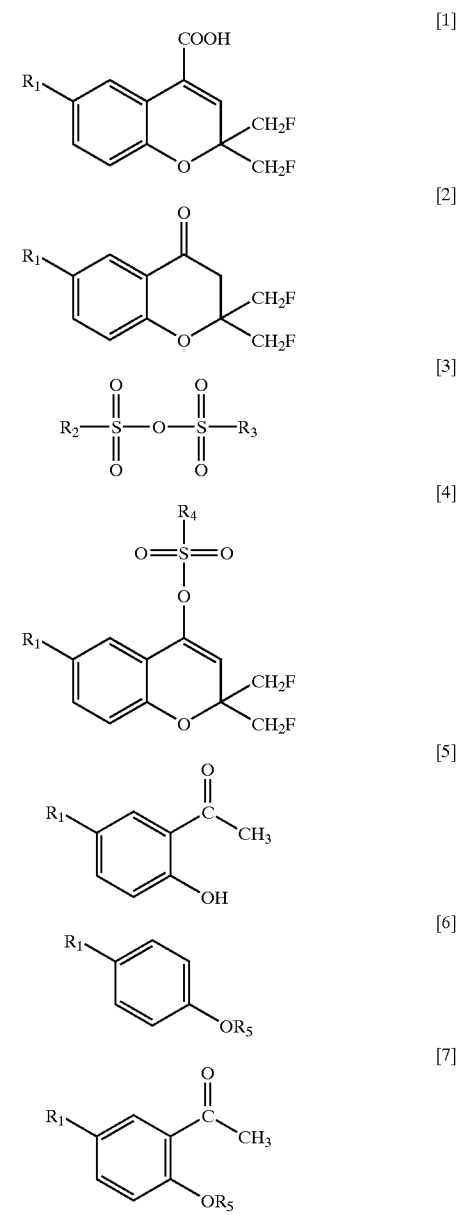

where $R_1$ is a perfluoroalkyl group that is represented by $C_nF_{2n+1}$ where n is an integer of 1–10 and that optionally has a branch in a carbon structure of the perfluoroalkyl group;

each of $R_2$ and $R_3$ is independently a lower perfluoroalkyl group that is represented by $C_nF_{2n+1}$ where n is an integer of 1–10 and that optionally has a branch in a carbon structure of the lower perfluoroalkyl group;

$R_4$ is identical with the $R_2$ or $R_3$; and $R_5$ is a straight-chain or non-straight-chain alkyl group having a carbon atom number of 1–20.

3. A process for producing a 2,2-bis(fluoromethyl)-6-(perfluoroalkyl)-2 H-1-benzopyran-4-carboxylic acid represented by the general formula [1], the process comprising the steps of:

(f) reacting a 4-perfluoroalkylphenol, represented by the general formula [8], with an alkylation agent, or reacting a 4-(perfluoroalkyl)halogenobenzene, represented by the general formula [9], with a metal alcoholate, thereby obtaining a 4-(perfluoroalkyl)alkoxybenzene, represented by the general formula [6];

(c) reacting the 4-(perfluoroalkyl)alkoxybenzene with acetic anhydride or an acyl halide in the presence of a Lewis acid, thereby obtaining a 2-alkoxy-5-(perfluoroalkyl) acetophenone represented by the general formula [7];

(d) dealkylating the 2-alkoxy-5-(perfluoroalkyl) acetophenone by a dealkylating agent, thereby obtaining a 2-hydroxy-5-(perfluoroalkyl)acetophenone represented by the general formula [5];

(e) reacting the 2-hydroxy-5-(perfluoroalkyl) acetophenone with 1,3-difluoroacetone in the presence of a base, thereby obtaining a 2,2-bis(fluoromethyl)-6-(perfluoroalkyl)-2 H-1-benzopyran-4-one represented by the general formula [2];

(a) reacting the 2,2-bis(fluoromethyl)-6-(perfluoroalkyl)-2 H-1-benzopyran-4-one with a perfluoroalkanesulfonic acid anhydride, represented by the general formula [3], in the presence of a base, thereby obtaining a perfluoroalkanesulfonic 2,2-bis(fluoromethyl)-6-(perfluoroalkyl)-2 H- 1-benzopyran-4-yl ester represented by the general formula [4]; and (b) reacting the benzopyranyl ester with carbon monoxide in the presence of a palladium complex compound and a base, thereby obtaining the carboxylic acid,

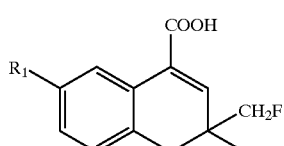

[1]

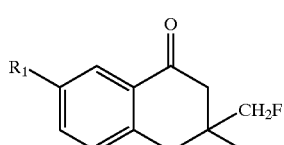

[2]

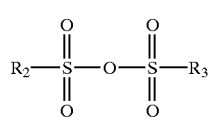

[3]

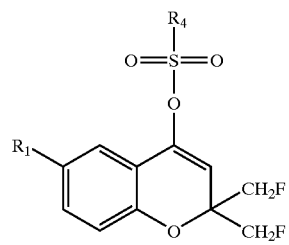

[4]

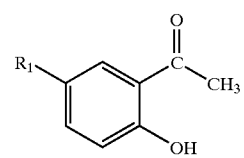

[5]

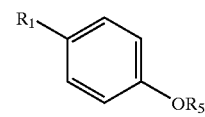

[6]

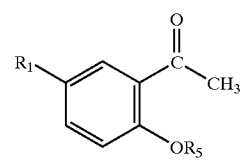

[7]

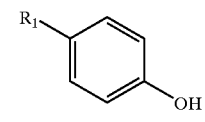

[8]

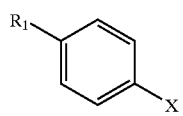

[9]

where $R_1$ is a perfluoroalkyl group that is represented by $C_nF_{2n+1}$ where n is an integer of 1–10 and that optionally has a branch in a carbon structure of the perfluoroalkyl group;

each of $R_2$ and $R_3$ is independently a lower perfluoroalkyl group that is represented by $C_nF_{2n+1}$ where n is an integer of 1–10 and that optionally has a branch in a carbon structure of the lower perfluoroalkyl group;

$R_4$ is identical with the $R_2$ or $R_3$;

$R_5$ is a straight-chain or non-straight-chain alkyl group having a carbon atom number of 1–20; and X is a fluorine, chlorine, bromine or iodine.

4. A process according to claim 1, wherein the 2,2-bis(fluoromethyl)-6-(perfluoroalkyl)-2 H-1-benzopyran-4-one of the step (a) is obtained by the step of (e) reacting a 2-hydroxy-5-(perfluoroalkyl) acetophenone, represented by the general formula [5], with 1,3-difluoroacetone in the presence of a base,

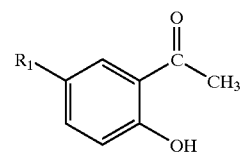

[5]

where $R_1$ is defined as above.

5. A process according to claim 1, wherein the base of the step (a) is 4-dimethylaminopyridine or 2,6-di-tert-butyl-4-methylpyridine.

6. A process according to claim 1, wherein the step (b) is conducted in the presence of a neutral inorganic salt.

7. A process according to claim 6, wherein the neutral inorganic salt is lithium chloride or potassium iodide.

8. A process according to claim 1, wherein the perfluoroalkanesulfonic acid anhydride of the step (a) is trifluoromethanesulfonic acid anhydride.

9. A process according to claim 1, wherein $R_1$ of the general formulas [1], [2] and [4] is a trifluoromethyl group.

10. A process for producing a 2-hydroxy-5-(perfluoroalkyl) acetophenone represented by the general formula [5], the process comprising the steps of:

(c) reacting a 4-(perfluoroalkyl)alkoxybenzene, represented by the general formula [6], with acetic anhydride or an acyl halide in the presence of a Lewis acid, thereby obtaining a 2-alkoxy-5-(perfluoroalkyl) acetophenone represented by the general formula [7]; and (d) dealkylating the 2-alkoxy-5-(perfluoroalkyl) acetophenone by a dealkylating agent, thereby obtaining the 2-hydroxy- 5-(perfluoroalkyl)acetophenone,

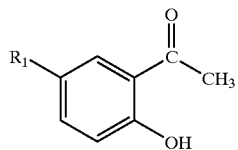
[5]

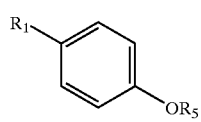
[6]

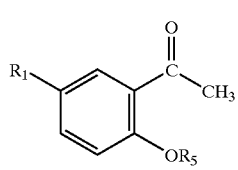
[7]

where $R_1$ is a perfluoroalkyl group that is represented by $C_nF_{2n+1}$ where n is an integer of 1–10 and that optionally has a branch in a carbon structure of the perfluoroalkyl group; and $R_5$ is a straight-chain or non-straight-chain alkyl group.

11. A process according to claim 10, wherein the 4-(perfluoroalkyl)alkoxybenzene of the step (c) is obtained by the step of (f) reacting a 4-perfluoroalkylphenol, represented by the general formula [8], with an alkylation agent, or reacting a 4-(perfluoroalkyl)halogenobenzene, represented by the general formula [9], with a metal alcoholate;

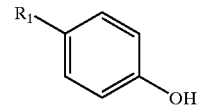
[8]

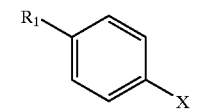
[9]

wherein X is a fluorine, chlorine, bromine or iodine.

12. A process according to claim 10, wherein the Lewis acid of the step (c) is trifluoromethanesulfonic acid.

13. A process according to claim 10, wherein the step (d) is conducted by reacting the 2-alkoxy-5-(perfluoroalkyl) acetophenone with boron tribromide, trimethylsilylchloride, or a metal salt of a thiol.

14. A process according to claim 13, wherein the step (d) is conducted by reacting the 2-alkoxy-5-(perfluoroalkyl) acetophenone with boron tribromide in methylene chloride.

15. A process according to claim 13, wherein the step (d) is conducted by reacting the 2-alkoxy-5-(perfluoroalkyl) acetophenone with trimethylsilylchloride in acetonitrile in the presence of sodium iodide.

16. A process according to claim 13, wherein the step (d) is conducted by reacting the 2-alkoxy-5-(perfluoroalkyl) acetophenone with a metal salt of a thiol in N,N-dimethylformamide.

17. A process according to claim 10, wherein $R_1$ of the general formulas [5], [6] and [7] is a trifluoromethyl group.

18. 2-methoxy-5-(trifluoromethyl)acetophenone represented by the following formula [10].

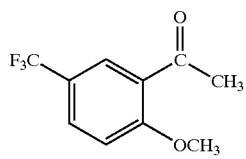
[10]

* * * * *